(12) United States Patent
Arcot-Krishnamurthy et al.

(10) Patent No.: US 8,219,210 B2
(45) Date of Patent: Jul. 10, 2012

(54) METHOD AND APPARATUS FOR IDENTIFICATION OF ISCHEMIC/INFARCTED REGIONS AND THERAPY OPTIMIZATION

(75) Inventors: Shantha Arcot-Krishnamurthy, Roseville, MN (US); Allan C. Shuros, St. Paul, MN (US); Jiang Ding, Maplewood, MN (US); Yinghong Yu, Shoreview, MN (US); Michael J. Stucky, Shoreview, MN (US); Chris Hartemink, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 721 days.

(21) Appl. No.: 11/541,837

(22) Filed: Oct. 2, 2006

(65) Prior Publication Data

US 2008/0082135 A1    Apr. 3, 2008

(51) Int. Cl.
*A61N 1/00*    (2006.01)
*A61B 5/04*    (2006.01)
(52) U.S. Cl. ............ 607/116; 607/2; 607/119; 600/509
(58) Field of Classification Search .............. 607/2, 116, 607/119; 600/509
See application file for complete search history.

(56) References Cited

U.S. PATENT DOCUMENTS

| | | | |
|---|---|---|---|
| 3,703,900 A | 11/1972 | Holznagel | |
| 3,716,059 A | 2/1973 | Welborn et al. | |
| 3,910,260 A | 10/1975 | Sarnoff et al. | |
| 4,004,577 A | 1/1977 | Sarnoff | |
| 4,562,846 A | 1/1986 | Cox et al. | |
| 4,679,144 A | 7/1987 | Cox et al. | |
| 4,924,875 A | 5/1990 | Chamoun | |
| 5,020,540 A | 6/1991 | Cahmoun | |
| 5,054,496 A | 10/1991 | Wen et al. | |
| 5,313,953 A | 5/1994 | Yomtov et al. | |
| 5,485,849 A | 1/1996 | Panescu et al. | |
| 5,505,202 A | 4/1996 | Mogi et al. | |
| 5,520,191 A | 5/1996 | Karlsson et al. | |
| 5,792,066 A | 8/1998 | Kwong | |
| 5,819,741 A | 10/1998 | Karlsson et al. | |
| 5,824,021 A | 10/1998 | Rise | |
| 5,833,621 A | 11/1998 | Panescu et al. | |
| 5,891,045 A | 4/1999 | Albrecht et al. | |
| 6,038,469 A | 3/2000 | Karlsson et al. | |
| 6,047,206 A | 4/2000 | Albrecht | |
| 6,141,588 A * | 10/2000 | Cox et al. ........................ | 607/9 |
| 6,171,256 B1 | 1/2001 | Joo et al. | |
| 6,217,525 B1 | 4/2001 | Medema et al. | |
| 6,381,493 B1 * | 4/2002 | Stadler et al. .................... | 607/9 |
| 6,514,195 B1 | 2/2003 | Ferek | |
| 6,604,000 B2 | 8/2003 | Lu | |

(Continued)

OTHER PUBLICATIONS

Shuros, A., "Ventricular Pre-Excitation Attenuates Cardiac Remodeling in a Swine Model of Myocardial Infarction", *American Heart Association Scientific Sessions*, Poster, (2005), 1 pg.

(Continued)

*Primary Examiner* — Nicole F Lavert
(74) *Attorney, Agent, or Firm* — Schwegman, Lundberg & Woessner, P.A.

(57) ABSTRACT

A method and apparatus is described for detecting and localizing areas of myocardial infarction or ischemia. By pacing sites in proximity to the infarcted or ischemic region with appropriately timed pacing pulses, the region is pre-excited in a manner that lessens the mechanical stress to which it is subjected, thus reducing the metabolic demand of the region and the stimulus for remodeling.

20 Claims, 6 Drawing Sheets

U.S. PATENT DOCUMENTS

| | | |
|---|---|---|
| 6,628,988 B2 | 9/2003 | Kramer et al. |
| 6,721,591 B2 | 4/2004 | Wei |
| 6,865,420 B1 * | 3/2005 | Kroll ............... 607/25 |
| 6,915,160 B2 | 7/2005 | Auricchio et al. |
| 6,937,899 B2 | 8/2005 | Sheldon et al. |
| 6,965,797 B2 | 11/2005 | Pastore et al. |
| 6,973,349 B2 | 12/2005 | Salo |
| 7,039,462 B2 | 5/2006 | Pastore et al. |
| 7,181,268 B2 | 2/2007 | Sheldon et al. |
| 7,181,269 B1 * | 2/2007 | Kroll ............... 600/517 |
| 7,215,997 B2 | 5/2007 | Yu et al. |
| 7,274,959 B1 * | 9/2007 | Wang et al. ............ 600/509 |
| 7,364,547 B2 | 4/2008 | Stahmann et al. |
| 7,415,307 B2 | 8/2008 | Sharma et al. |
| 7,512,439 B1 | 3/2009 | Farazi |
| 7,577,478 B1 | 8/2009 | Kroll et al. |
| 2002/0111551 A1 | 8/2002 | Erlach et al. |
| 2003/0013974 A1 * | 1/2003 | Natarajan et al. ......... 600/481 |
| 2003/0060854 A1 | 3/2003 | Zhu |
| 2004/0054381 A1 | 3/2004 | Pastore et al. |
| 2005/0065568 A1 | 3/2005 | Liu et al. |
| 2005/0159666 A1 | 7/2005 | Pearce et al. |
| 2005/0177195 A1 | 8/2005 | Salo |
| 2005/0256417 A1 | 11/2005 | Fischell et al. |
| 2005/0283195 A1 | 12/2005 | Pastore et al. |
| 2006/0009811 A1 | 1/2006 | Sheldon et al. |
| 2006/0052717 A1 | 3/2006 | Mugler et al. |
| 2006/0116593 A1 | 6/2006 | Zhang et al. |
| 2006/0253044 A1 | 11/2006 | Zhang |
| 2006/0259087 A1 | 11/2006 | Baynham et al. |
| 2006/0287684 A1 | 12/2006 | Baynham et al. |
| 2007/0038256 A1 | 2/2007 | Maschke |
| 2007/0043393 A1 | 2/2007 | Brockway et al. |
| 2007/0054871 A1 | 3/2007 | Pastore et al. |
| 2007/0093720 A1 | 4/2007 | Fischell et al. |
| 2007/0129639 A1 | 6/2007 | Zhang |
| 2007/0150005 A1 | 6/2007 | Sih et al. |
| 2007/0162081 A1 | 7/2007 | Yu et al. |
| 2007/0179392 A1 | 8/2007 | Zhang |
| 2007/0203524 A1 | 8/2007 | Sheldon et al. |
| 2007/0208263 A1 | 9/2007 | John et al. |
| 2007/0299356 A1 | 12/2007 | Wariar et al. |
| 2008/0081354 A1 | 4/2008 | Qu et al. |
| 2008/0139954 A1 | 6/2008 | Day et al. |
| 2008/0177194 A1 | 7/2008 | Zhang et al. |
| 2008/0188762 A1 | 8/2008 | John et al. |
| 2008/0188763 A1 | 8/2008 | John et al. |
| 2008/0228094 A1 | 9/2008 | Audet et al. |
| 2009/0048528 A1 | 2/2009 | Hopenfeld et al. |
| 2009/0082682 A1 | 3/2009 | Fischell et al. |
| 2009/0171228 A1 | 7/2009 | Fischell et al. |
| 2009/0177103 A1 | 7/2009 | Bharmi |

OTHER PUBLICATIONS

Shuros, Allan C., et al., "Ventricular Preexcitation Modulates Strain and Attenuates Cardiac Remodeling in a Swine Model of Myocardial Infarction", *Circulation: Journal of the American Heart Association*, (Sep. 4, 2007), 9 pgs.

Zhang, Y., et al., "Left ventricular systolic asynchrony after acute myocardial infarction in patients with narrow QRS complexes", *American Heart Journal*, 149(3), (Mar. 2005), 497-503.

\* cited by examiner

METHOD AND APPARATUS FOR IDENTIFICATION OF ISCHEMIC/INFARCTED REGIONS AND THERAPY OPTIMIZATION

RELATED CASES

This application is related to U.S. Pat. Nos. 6,628,988, 6,973,349, 6,915,160 and 6,965,797 and to U.S. patent application Ser. No. 11/427,517, still pending, filed on Jun. 29, 2006, all of which are hereby incorporated by reference in their entirety.

FIELD OF THE INVENTION

This invention pertains to cardiac rhythm management devices such as pacemakers and other implantable devices.

BACKGROUND

A myocardial infarction (MI) is the irreversible damage done to a segment of heart muscle by ischemia, where the myocardium is deprived of adequate oxygen and metabolite removal due to an interruption in blood supply. It is usually due to a sudden thrombotic occlusion of a coronary artery, commonly called a heart attack. If the coronary artery becomes completely occluded and there is poor collateral blood flow to the affected area, a transmural or full-wall thickness infarct can result in which much of the contractile function of the area is lost. Over a period of one to two months, the necrotic tissue heals, leaving a scar. The most extreme example of this is a ventricular aneurysm where all of the muscle fibers in the area are destroyed and replaced by fibrous scar tissue.

Even if the ventricular dysfunction as a result of the infarct is not immediately life-threatening, a common sequela of a transmural myocardial infarction, or any major MI, especially in the left ventricle, is heart failure brought about by ventricular remodeling. Ventricular remodeling is a physiological process in response to the hemodynamic effects of the infarct that causes changes in the shape and size of the ventricle. Remodeling is initiated in response to a redistribution of cardiac stress and strain caused by the impairment of contractile function in the infarcted area as well as in nearby and/or interspersed viable myocardial tissue with lessened contractility due to the infarct. Following an MI, the infarcted area includes tissue undergoing ischemic necrosis and is surrounded by normal myocardium. Until scar tissue forms and even after it forms, the area around the infarcted area is particularly vulnerable to the distending forces within the ventricle and undergoes expansion over a period of hours to days. Over the next few days and months after scar tissue has formed, global remodeling and chamber enlargement occur due to complex alterations in the architecture of the ventricle involving both infarcted and non-infarcted areas.

Remodeling is thought to be the result of a complex interplay of hemodynamic, neural, and hormonal factors that occur primarily in response to myocardial wall stress. One physiological compensatory mechanism that acts to increase cardiac output is increased diastolic filling pressure of the ventricles as an increased volume of blood is left in the lungs and venous system. This increases the preload, which is the degree to which the ventricles are stretched by the volume of blood in the ventricles at the end of diastole. An increase in preload causes an increase in contractility and resulting increase in stroke volume during systole, a phenomenon known as the Frank-Starling principle. The ventricular dilation resulting from the increased preload causes increased ventricular wall stress at a given systolic pressure in accordance with Laplace's law. Along with the increased pressure-volume work done by the ventricle, this acts as a stimulus for compensatory hypertrophy of the ventricular myocardium. Hypertrophy can increase systolic pressures but, if the hypertrophy is not sufficient to meet the increased wall stress, further and progressive dilation results. This non-compensatory dilation causes wall thinning and further impairment in left ventricular function. It also has been shown that the sustained stresses causing hypertrophy may induce apoptosis (i.e., programmed cell death) of cardiac muscle cells. Thus, although ventricular dilation and hypertrophy may at first be compensatory and increase cardiac output, the process ultimately results in further deterioration and dysfunction. It has been found that the extent of left ventricular remodeling in the late period after an infarction, as represented by measurements of end-systolic and end-diastolic left ventricular volumes, is an even more powerful predictor of subsequent mortality than the extent of coronary artery disease.

SUMMARY

The part of the myocardium that is most vulnerable to the post-infarct remodeling process is the infarct region, which is an area that includes sites in and around the infarct where the myocardial fibers are still intact but contractile function is impaired. The infarct region is thus the area most likely to undergo the progressive non-compensatory dilation described above with wall thinning and further impairment of function. By pacing sites in proximity to the infarct with appropriately timed pacing pulses, the infarct region is pre-excited in a manner that lessens the mechanical stress to which it is subjected, thus reducing the stimulus for remodeling. Such pre-excitation pacing may also be beneficially applied to reduce stress at a region that is ischemic but not yet infarcted by reducing the metabolic demand of the affected myocardial region and thereby reducing the chances of permanent damage.

Described herein are methods and apparatus for detecting and localizing ischemic or infarcted myocardial regions implementable in an implantable cardiac device. After such detection and localization, the implantable cardiac device may be configured to alert clinical personnel so that appropriate therapy may be initiated and/or configured to automatically initiate and/or optimize pre-excitation pacing therapy.

DETAILED DESCRIPTION

Figure 1:
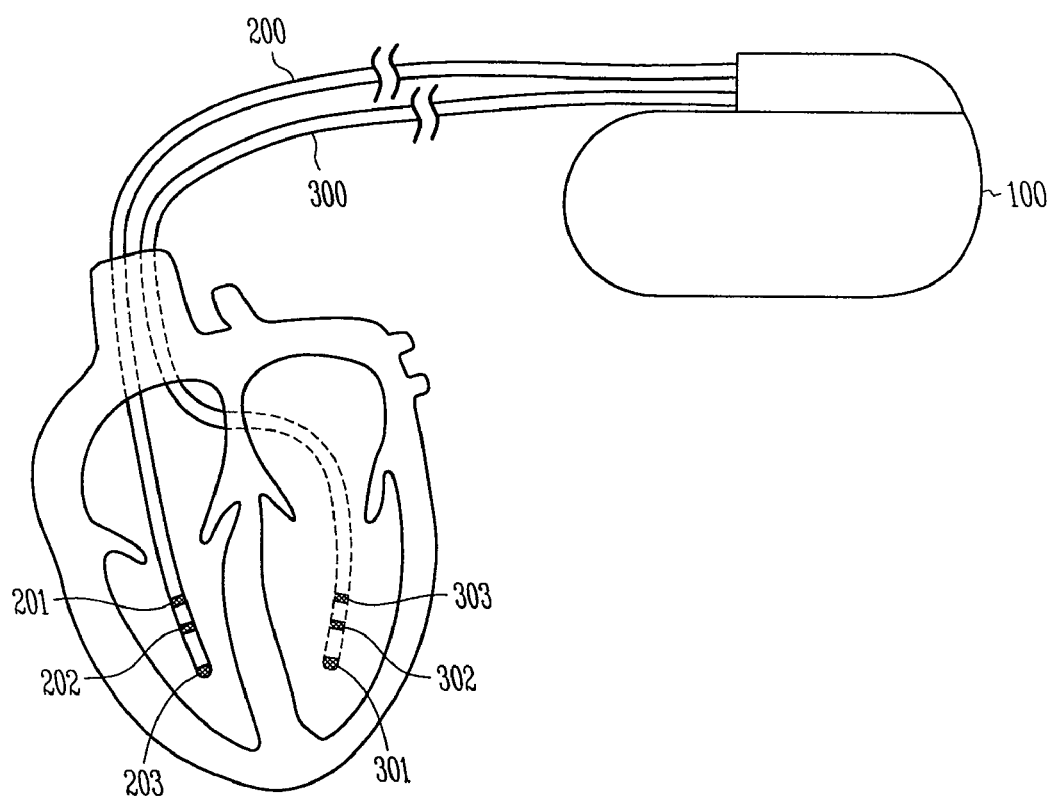
FIG. 1 illustrates the physical configuration of an exemplary pacing device.

When the blood supply to a region of the myocardium is compromised, the supply of oxygen and other nutrients can become inadequate for enabling the metabolic processes of the cardiac muscle cells to maintain their normal polarized state. An ischemic region of the heart therefore becomes abnormally depolarized during at least part of the cardiac cycle and causes a current to flow between the ischemic region and the normally polarized regions of the heart, referred to as a current of injury. A current of injury may be produced by an infarcted region that becomes permanently depolarized or by an ischemic region that remains abnormally depolarized during all or part of the cardiac cycle. Ischemia and infarction can also affect the magnitude of depolarization and the velocity at which it travels through the myocardium. All of these effects result in abnormal changes in the electrical potentials produced by cardiac excitation as reflected by either a surface electrocardiogram or an intracardiac electrogram. Ischemia and infarction also lessens the excitability of the myocardium and negatively affects mechanical contraction.

The changes to the electrical and mechanical properties of the myocardium that occur as a result of infarction or ischemia described above are locally measurable changes. That is, sensors for producing signals that enable measurement of such changes may be physically disposed near different myocardial regions, and a sensor located closer to an infarcted/ischemic region will produce a signal that results in a measured change of greater magnitude than a sensor located farther away. For example, in the case of an electrode for sensing cardiac electrograms, the closer the sensing electrode is to an infarcted or ischemic region, the more pronounced will be the changes in the electrogram due to myocardial ischemia or infarction. Locally measurable phenomena affected by ischemia or infarction present a way by which an implantable device may detect myocardial ischemia/infarction and localize the ischemic/infarcted region(s). Such a device may be configured with a plurality of sensors adapted to be disposed near different myocardial regions. The sensors may be electrodes for detecting cardiac electrical activity, mechanical sensors for detecting myocardial displacement or strain, and/or sensors for detecting other electrical, mechanical, or chemical properties that are locally affected by myocardial ischemia or infarction. The device may then be configured to continuously or periodically measure one or more characteristics as derived from the sensor signals over time and establish baseline values for the measured characteristics. After such baseline values are established, the device may continue to monitor the characteristic(s) and detect myocardial ischemia/infarction when a deviation from the baseline in one or more characteristics occurs above a specified threshold. The device may then localize the ischemic/infarcted region(s) by analyzing the magnitudes of the measured characteristics as derived from differently located sensors. After detection and localization of myocardial ischemia or infarction, the device may be configured to issue an alert by various means such as transmission of an alert message to a remote monitor via telemetry, which message may then be conveyed over a network to a patient management server. Clinicians may then use the information collected by the implantable device, including the localization of the ischemic/infarcted region, to deliver appropriate treatment. In another embodiment, the implantable device may be configured to automatically initiate or modify a treatment deliverable by the device itself in accordance with detection and localization of myocardial ischemia or infarction. As described below, one such treatment is pre-excitation pacing of particular myocardial sites in order to lessen the mechanical stress to which such sites are subjected during myocardial contraction. After localizing the ischemic/infarcted region, the device may further be configured to select one or more particular sites for delivering pre-excitation pacing using the same or different electrodes as those used for sensing. In various embodiments, the device could alternatively or additionally be configured with other treatment modalities for responding to myocardial ischemia/infarction such as drug delivery or other types of electrical therapy.

Pre-Excitation Pacing for Reducing Stress

The degree to which a heart muscle fiber is stretched before it contracts is termed the preload, while the degree of tension or stress on a heart muscle fiber as it contracts is termed the afterload. The maximum tension and velocity of shortening of a muscle fiber increases with increasing preload. When a myocardial region contracts late relative to other regions, the contraction of those other regions stretches the later contracting region and increases its preloading, thus causing an increase in the contractile force generated by the region. Conversely, a myocardial region that contracts earlier relative to other regions experiences decreased preloading and generates less contractile force. Because pressure within the ventricles rises rapidly from a diastolic to a systolic value as blood is pumped out into the aorta and pulmonary arteries, the parts of the ventricles that contract earlier during systole do so against a lower afterload than do parts of the ventricles contracting later. Thus, if a ventricular region can be made to contract earlier than other parts of the ventricle, it will be subjected to both a decreased preload and afterload which decreases the mechanical stress experienced by the region relative to other regions during systolic contraction. The region will also do less work thus lessening its metabolic demands and the degree of any ischemia that may be present.

If the region around an infarct were made to contract during early systole, it would be subjected to less distending forces and less likely to undergo expansion, especially during the period immediately after a myocardial infarction. Similarly, if a region that is ischemic but not yet infarcted were made to contract during early systole, the reduced mechanical stress to which the region is subjected would lessen the metabolic demand of the region and reduce the chances of permanent damage. In order to cause early contraction and lessened stress, electro-stimulatory pacing pulses may be delivered to one or more sites in or around the infarct or ischemic region in a manner that pre-excites those sites relative to the rest of the ventricle. (As the term is used herein, a pacing pulse is any electrical stimulation of the heart of sufficient energy to initiate a propagating depolarization, whether or not intended to enforce a particular heart rate.) In a normal heartbeat, the specialized His-Purkinje conduction network of the heart rapidly conducts excitatory impulses from the sino-atrial node to the atrio-ventricular node, and thence to the ventricular myocardium to result in a coordinated contraction of both ventricles. Artificial pacing with an electrode fixed into an area of the myocardium does not take advantage of the heart's normal specialized conduction system for conducting excitation throughout the ventricles because the specialized conduction system can only be entered by impulses emanating from the atrio-ventricular node. Thus the spread of excitation from a ventricular pacing site must proceed only via the much slower conducting ventricular muscle fibers, resulting in the part of the ventricular myocardium stimulated by the pacing electrode contracting well before parts of the ventricle located more distally to the electrode.

Pre-excitation of a paced site relative to other sites can be used to deliberately change the distribution of wall stress experienced by the ventricle during the cardiac pumping cycle in order to prevent or reduce the remodeling that would otherwise occur and/or reduce the chances of permanent damage due to ischemia. Pacing therapy to unload an infarcted/ischemic region may be implemented by pacing the ventricles at a single site in proximity to the infarcted/ischemic region or by pacing at multiple ventricular sites in such proximity. In the latter case, the pacing pulses may be delivered to the multiple sites simultaneously or in a defined pulse output sequence. The single-site or multiple site pacing may be performed in accordance with a bradycardia pacing algorithm such as an inhibited demand mode or a triggered mode.

Exemplary Implantable Device

In an exemplary embodiment as described below, an implantable cardiac device is configured with multiple electrodes that may be used for sensing cardiac electrograms and/or delivering pacing pulses at selected multiple sites. The device may further include mechanical sensors by which mechanical characteristics of the myocardium may be measured at multiple sites. The control circuitry of the exemplary device may be configured to measure one or more electrical and/or mechanical characteristics at selected multiple sites, establish baseline values for the characteristics, and monitor for changes in the characteristics to detect and localize myocardial ischemia/infarction. Detection of myocardial ischemia/infarction may be communicated by the device to a remote monitor. The device may be further configured to initiate, cease, or modify the delivery of pre-excitation pacing to reduce the mechanical stress of ischemic/infarcted regions in accordance with information derived from the measured characteristics.

FIG. 1 shows an implantable cardiac device 100 for delivering pre-excitation therapy to an infarct region as well as possibly other types of pacing therapy. Implantable pacing devices are typically placed subcutaneously or submuscularly in a patient's chest with leads threaded intravenously into the heart to connect the device to electrodes disposed within a heart chamber that are used for sensing and/or pacing of the chamber. Electrodes may also be positioned on the epicardium by various means. A programmable electronic controller causes the pacing pulses to be output in response to lapsed time intervals and/or sensed electrical activity (i.e., intrinsic heart beats not as a result of a pacing pulse). The device senses intrinsic cardiac electrical activity through one or more sensing channels, each of which incorporates one or more of the electrodes. In order to excite myocardial tissue in the absence of an intrinsic beat, pacing pulses with energy above a certain threshold are delivered to one or more pacing sites through one or more pacing channels, each of which incorporates one or more of the electrodes. FIG. 1 shows the exemplary device having two leads 200 and 300, each of which is a multi-polar (i.e., multi-electrode) lead having electrodes 201-203 and 301-303, respectively. The electrodes 201-203 are disposed in the right ventricle in order to excite or sense right ventricular or septal regions, while the electrodes 301-303 are disposed in the coronary sinus in order to excite or sense regions of the left ventricle. Other embodiments may use any number of electrodes in the form of unipolar and/or multi-polar leads in order to excite different myocardial sites. As explained below, once the device and leads are implanted, the pacing and/or sensing channels of the device may be configured with selected ones of the multiple electrodes in order to selectively pace or sense a particular myocardial site(s).

Figure 2:
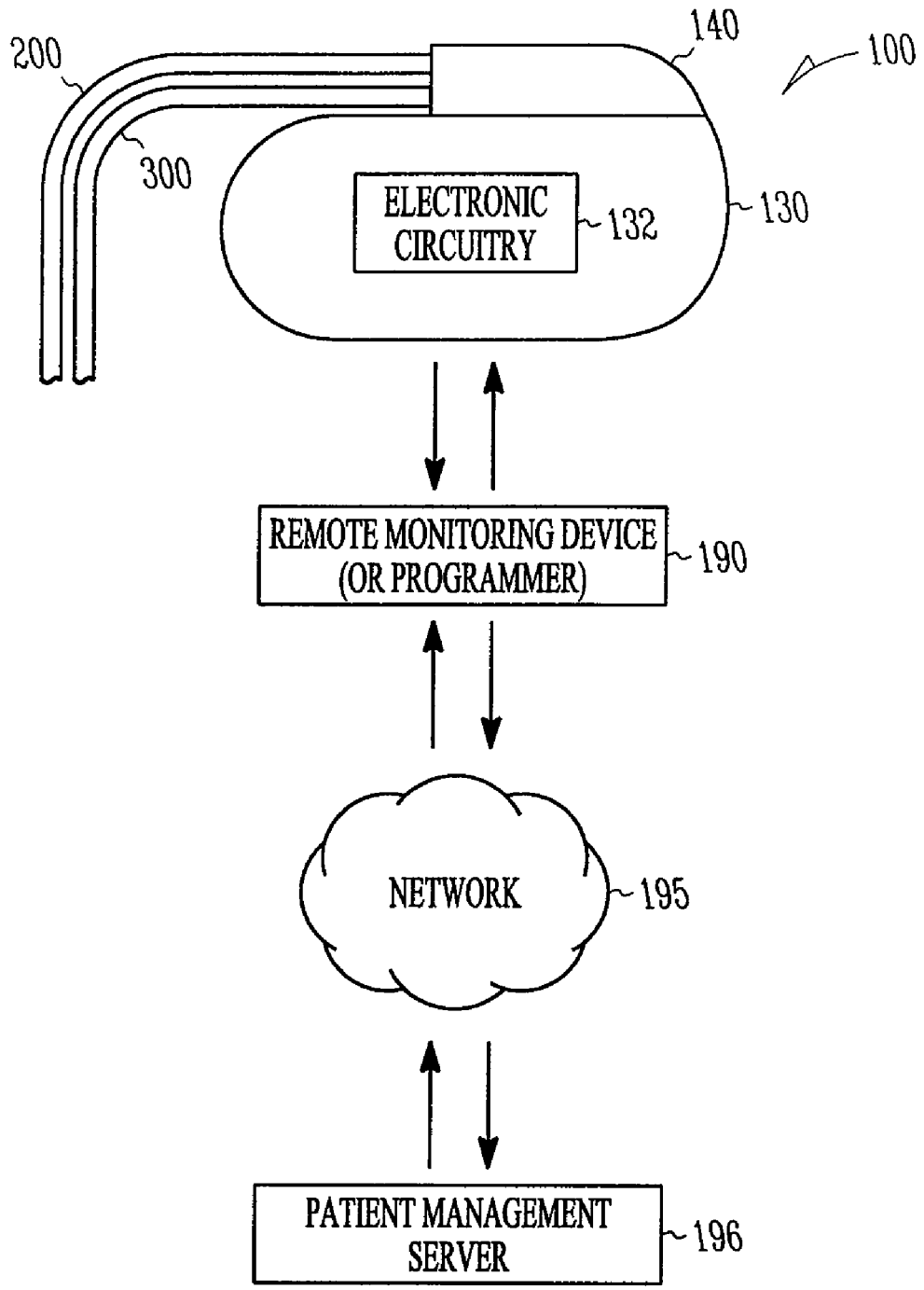
FIG. 2 shows the components of an exemplary device.

FIG. 2 shows the components of the implantable device 100 in more detail as well as an exemplary monitoring/programming system. The implantable device 100 includes a hermetically sealed housing 130 that is placed subcutaneously or submuscularly in a patient's chest. The housing 130 may be formed from a conductive metal, such as titanium, and may serve as an electrode for delivering electrical stimulation or sensing in a unipolar configuration. A header 140, which may be formed of an insulating material, is mounted on the housing 130 for receiving leads 200 and 300 which may be then electrically connected to pulse generation circuitry and/or sensing circuitry. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device 190. An external programmer wirelessly communicates with the device 100 and enables a clinician to receive data and modify the programming of the controller. A remote monitoring device also communicates via telemetry with the device 100 and may be further interfaced to a network 195 (e.g., an internet connection) for communicating with a patient management server 196 that allows clinical personnel at remote locations to receive data from the remote monitoring device as well as issue commands. The controller may be programmed such when particular conditions are detected by the monitoring circuitry (such as when a measured parameter exceeds or falls below a specified limit value), the device transmits an alarm message to the remote monitoring device and to the patient management server to alert clinical personnel.

Figure 3:
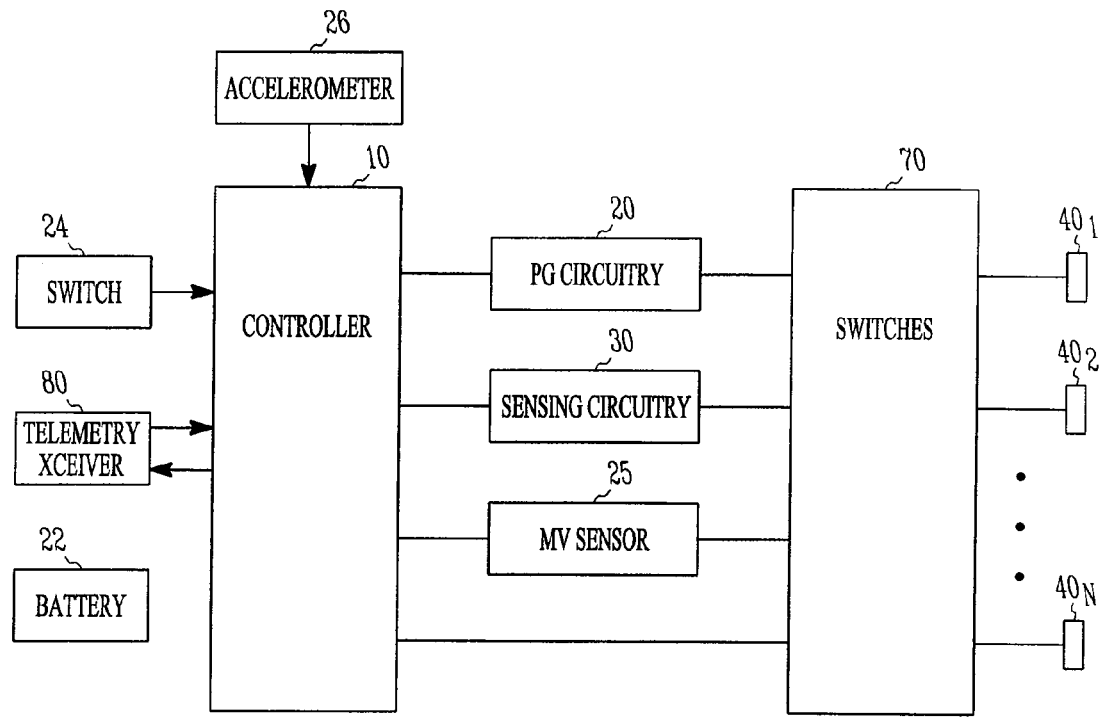
FIG. 3 is a block diagram of the electronic circuitry of an exemplary device.

A block diagram of the circuitry 132 is illustrated in FIG. 3. A battery 22 supplies power to the circuitry. The controller 10 controls the overall operation of the device in accordance with programmed instructions and/or circuit configurations. The controller may be implemented as a microprocessor-based controller and include a microprocessor and memory for data and program storage, implemented with dedicated hardware components such as ASICs (e.g., finite state machines), or implemented as a combination thereof. The controller also includes timing circuitry such as external clocks for implementing timers used to measure lapsed intervals and schedule events. As the term is used herein, the programming of the controller refers to either code executed by a microprocessor or to specific configurations of hardware components for performing particular functions. Interfaced to the controller are sensing circuitry 20 and pulse generation circuitry 30 by which the controller interprets sensing signals and controls the delivery of paces in accordance with a pacing mode. The sensing circuitry 20 receives atrial and/or ventricular electrogram signals from sensing electrodes and includes sensing amplifiers, analog-to-digital converters for digitizing sensing signal inputs from the sensing amplifiers, and registers that can be written to for adjusting the gain and threshold values of the sensing amplifiers. The pulse generation circuitry 30 delivers pacing pulses to pacing electrodes disposed in the heart and includes capacitive discharge pulse generators, registers for controlling the pulse generators, and registers for adjusting pacing parameters such as pulse energy (e.g., pulse amplitude and width). The device allows adjustment of the pacing pulse energy in order to ensure capture of myocardial tissue (i.e., initiating of a propagating action potential) by a pacing pulse. Myocardial sites in proximity to an infarct or within ischemic regions may be less excitable than normal and require an increased pacing energy in order to achieve capture. Pacing pulse energies for pre-exciting infarcted/ischemic regions may be adjusted by programming the device via the telemetry interface in accordance with electrophysiological testing to determine an appropriate pacing pulse energy or may be adjusted automatically with an autocapture function such as described in U.S. patent application Ser. No. 11/427,517, filed on Jun. 29, 2006. The pulse generation circuitry may also include a shocking pulse generator for delivering a defibrillation/cardioversion shock via a shock electrode upon detection of a tachyarrhythmia. A telemetry transceiver 80 is interfaced to the controller which enables the controller to communicate with an external programmer and/or a remote monitoring unit. A magnetically or tactilely actuated switch 24 is also shown as interfaced to the controller to allow the patient to signal certain conditions or events to the implantable device.

A pacing channel is made up of a pulse generator connected to an electrode, while a sensing channel is made up of a sense amplifier connected to an electrode. Shown in the figure are electrodes $40_1$ through $40_N$ where N is some integer. The electrodes may be on the same or different leads and are electrically connected to a MOS switch matrix 70. The switch matrix 70 is controlled by the controller and is used to switch selected electrodes to the input of a sense amplifier or to the output of a pulse generator in order to configure a sensing or pacing channel, respectively. The device may be equipped with any number of pulse generators, amplifiers, and electrodes that may be combined arbitrarily to form sensing or pacing channels. The switch matrix 70 allows selected ones of the available implanted electrodes to be incorporated into sensing and/or pacing channels in either unipolar or bipolar configurations. A bipolar sensing or pacing configuration refers to the sensing of a potential or output of a pacing pulse between two closely spaced electrodes, where the two electrodes are usually on the same lead (e.g., a ring and tip electrode of a bipolar lead or two selected electrodes of a multi-polar lead). A unipolar sensing or pacing configuration is where the potential sensed or the pacing pulse output by an electrode is referenced to the conductive device housing or another distant electrode.

The device illustrated in FIG. 3 may be configured with multiple sensing and/or pacing channels that may be either atrial or ventricular channels depending upon the location of the electrode. The device is therefore capable of delivering single-site or multiple site ventricular pre-excitation pacing for purposes of stress reduction as well as conventional pacing. The switch matrix allows particular myocardial sites to be pre-excited for purposes of stress reduction by selecting the appropriately disposed electrode(s) to be incorporated into a pacing channel used to deliver pre-excitation pacing. Configuration of pacing and sensing channels may be performed via an external programmer communicating through the telemetry interface or, as discussed below, may be performed automatically by the controller executing a configuration algorithm.

Pre-excitation pacing may be delivered as single-site pacing, biventricular pacing where one of the ventricles is pre-excited relative to the other as determined by a programmed biventricular offset interval, or delivered as multi-site ventricular pacing. In the case where the pre-excitation pacing is delivered at multiple sites, the sites may be paced simultaneously or in accordance with a particular pulse output sequence that specifies the order and timing in which the sites are to be paced during a single beat. When an electrogram signal in an atrial or ventricular sensing channel exceeds a specified threshold, the controller detects an atrial or ventricular sense, respectively, which pacing algorithms may employ to trigger or inhibit pacing. The controller is capable of operating the device in a number of programmed modes where a programmed mode defines how pacing pulses are output in response to sensed events and expiration of time intervals. Pre-excitation pacing of one or more ventricular sites in proximity to an infarct may be delivered in conjunction with a bradycardia pacing mode, which refers to a pacing algorithm that enforces a certain minimum heart rate, and may include or not include pacing pulses delivered to the atria or ventricles for other purposes (e.g., treatment of bradycardia). Inhibited demand bradycardia pacing modes utilize escape intervals to control pacing in accordance with sensed intrinsic activity. In an inhibited demand ventricular pacing mode, the ventricle is paced during a cardiac cycle only after expiration of a defined escape interval during which no intrinsic beat by the chamber is detected. For example, a ventricular escape interval can be defined between ventricular events so as to be restarted with each ventricular sense or pace, referred to as a ventriculo-ventricular or VV interval. The inverse of this escape interval is the minimum rate at which the pacemaker will allow the ventricles to beat, sometimes referred to as the lower rate limit (LRL). Paces may also be delivered in a rate-adaptive pacing mode where the VV interval and/or other escape intervals are modified in accordance with a measured exertion level such as with accelerometer 26 or minute ventilation sensor 25. In atrial tracking and AV sequential pacing modes, another ventricular escape interval is defined between atrial and ventricular events, referred to as the atrio-ventricular or AV interval. The atrio-ventricular interval is triggered by an atrial sense or pace and stopped by a ventricular sense or pace. A ventricular pace is delivered upon expiration of the atrio-ventricular interval if no ventricular sense occurs before the expiration. Because it is only paced beats that pre-excite the infarcted/ischemic region, it may be desirable to decrease the AV interval to be below the intrinsic PR interval (i.e., the normal time for an intrinsic ventricular beat to occur after an atrial sense or pace) and/or increase the LRL to be above the patient's normal resting heart rate. Delivering pre-excitation with a shortened AV or VV interval also facilitates pre-excitation by allowing the depolarization to spread beyond the pre-excited site and excite the rest of the myocardium without interference from intrinsic excitation.

In order to pre-excite an ischemic/infarcted region, the region must be identified anatomically so that one or more pacing electrodes can be placed in proximity thereto. An area of infarct or ischemia can be identified by a number of means, including ultrasonic imaging, PET scans, CT scans, thallium scans, and MRI perfusion scans. After implantation and appropriate placement of electrodes, the device may then be programmed to be configured with appropriate sensing and pacing channels to deliver pre-excitation pacing to one or more sites in proximity to the identified ischemic/infarcted region accordance with a particular pacing mode. As discussed below, infarcted/ischemic regions may also be identified from data collected by the implantable device to enable automatic reconfiguration of pacing channels to deliver pre-excitation pacing.

The implantable device may also incorporate autocapture, autothreshold, and reconfiguration functionality described in U.S. patent application Ser. No. 11/427,517, which are especially useful for the delivery of pre-excitation pacing to an infarct region because the excitability characteristics of an infarcted/ischemic region may change over time. The device thus may be configured to automatically adjust pre-excitation pacing pulse energies and/or pre-excitation pacing sites in order maintain capture by the pre-excitation pacing pulses. In order to determine whether or not a pacing pulse has achieved capture, a capture verification test is performed in which an evoked response to the pre-excitation pacing pulse detected. An evoked response sensing channel is configured using the switch matrix to select an appropriate electrode which may be the same electrode used to deliver the pacing pulse or another electrode disposed near the pacing site. Verifying capture by the pacing pulse involves comparing the evoked response electrogram signal following the pace to a predetermined threshold, which may be performed by the controller or other dedicated circuitry. If the evoked response electrogram signal exceeds the threshold, capture is presumed to have occurred. Upon detection of capture failure, or in order to determine a minimum pacing energy, an autothreshold procedure may be performed by the device in which a minimum pacing threshold is determined. The pacing pulse energy is then adjusted accordingly to match the determined minimum pacing threshold with an appropriate safety margin. Automatic pacing electrode reconfiguration, entailing changing pacing sites until one is found for which capture is possible, may be performed upon detection of a loss of capture and when the autocapture function is unable to adjust the pacing pulse energy for a particular pacing site to a level adequate to regain capture using the available pacing pulse amplitudes and widths supported by the device. The pacing electrode reconfiguration algorithm can also be performed periodically or upon command. Such reconfiguration may be performed in accordance with a preprogrammed ordered list of the available pacing electrodes that lists the electrodes in a preferred order of use as determined by clinical testing in order to ensure that the reconfiguration algorithm selects the most optimum pacing location for pre-excitation pacing. The ordered list of available electrodes may also be generated and/or updated automatically by the device in accordance with regions of ischemia/infarction that are identified from sensing data as described below.

The switch matrix allows multiple sensing channels to be configured using the available electrodes in order to generate electrogram signals from multiple cardiac sites. Such electrogram signals may be used to generate atrial and ventricular senses for controlling pacing and, by measuring the intervals between such senses, for determining atrial and ventricular rates in order to detect arrhythmias. As will be subsequently discussed in more detail, the electrogram signals generated from multiple sites also exhibit characteristics that may be analyzed in order to detect and localize ischemic or infarcted regions.

Detection and Localization of Ischemic/Infarcted Regions

As discussed above, ischemia/infarction causes changes in the electrical properties of myocardial tissue that are reflected in particular characteristics of electrograms recorded by an electrode near the ischemic/infarcted region. An implantable device configured with sensing electrodes at multiple sites may be programmed to measure these characteristics and thereby detect and localize areas of ischemia or infarction. Such sensing electrodes may be strategically disposed at different myocardial sites, where the electrodes are incorporated into one or more leads. In order to dispose an adequate number of electrodes at selected sites, the sensing electrodes are preferably incorporated into one or more multi-polar leads having electrodes sufficiently spaced apart to span a variety of different ventricular locations. The electrodes may be epicardially or endocardially disposed. The electrodes are configured into sensing channels by the switch matrix which connects them to sensing amplifiers. If there are more electrodes than available sensing amplifiers, the switch matrix may be operated to alternate between different sets of the electrodes during different cardiac cycles.

From each of the electrogram signals generated by the multiple sensing electrodes, the implantable device is programmed to measure one or more characteristics that are affected by ischemia or infarction on a continual or periodic basis. The electrograms may be intrinsic or evoked response electrograms. The measured characteristics are trended over time in order to establish baseline values that can be compared with in order to detect changes in the characteristics indicative of ischemia or infarction. One example of a locally measurable characteristic affected by ischemia/infarction is the intrinsic activation time (IAT) measured at an electrode, defined as the time between a reference point (e.g., the time of an atrial pace or sense) and a fiducial point extracted from electrogram of that electrode. Examples of such fiducial points could include the time of zero-crossing between the positive and negative peak of a bipolar electrogram, the time of largest (negative/positive) peak of a unipolar electrogram, the time of maximal rate of change of voltage of a unipolar electrogram, or the time of specified threshold-crossing of a unipolar or bipolar electrogram where the threshold can either be fixed or patient-specific. Other measurable characteristics locally affected by ischemia/infarction include the time interval between the start of depolarization and the end of repolarization, the duration or width of depolarization, the amplitude of the electrogram signal, and different morphological features of the electrogram as detected by correlation with a patient-specific template waveform.

Figure 4:
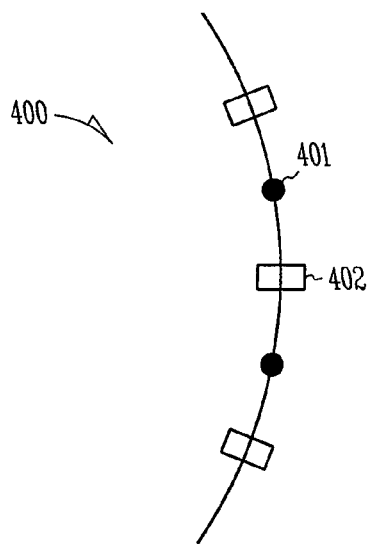
FIG. 4 illustrates an embodiment of a multi-polar lead.

The device may also be configured with other sensing modalities to measure other kinds of characteristics of myocardial tissue affected by ischemia or infarction. For example, mechanical variables of different ventricular regions such as displacement and strain may be measured by appropriately placed accelerometers, sonomicrometry crystals, or other strain measuring devices. Characteristics such as amplitude, slope and time to reach a maximum or minimum peak may then be extracted from the accelerometer signals. Impedance measurements performed by electrodes may also be used for measuring myocardial displacement or strain. FIG. 4 shows an embodiment of a multi-polar lead 400 with a plurality of electrodes 401 and accelerometers 402 along its length for measuring both electrical and mechanical characteristics of selected regions. Both the accelerometers and electrodes may be connected to the sensing circuitry by the switch matrix. Another measurable characteristic locally affected by ischemia/infarction is the pacing energy necessary to achieve capture at an electrode site, which energy can be expected to increase. The device may periodically or otherwise measure the capture threshold at the different electrode sites by incorporating the electrodes into pacing channels and performing the autothreshold procedure described above.

In order to detect ischemia/infarction, the measured characteristics from each electrode or other sensor are trended over time so that baseline values may be established. A measure of the normal dispersion of the characteristics' values, such as variance or standard deviation, may also be computed. The device may then monitor the measured characteristics at each electrode for acute changes. Ischemia/infarction is then detected if such an acute change deviates from the characteristic's baseline value by a specified threshold amount. (In order to confirm that a detected acute change is not due to some type of lead failure, a lead impedance or other test may also be performed after such detection.) The closer an electrode is to an ischemic/infarcted region, the more affected will be the characteristic measured by the electrode. This allows the location and/or size of an ischemic/infarcted region to be estimated from the number and location of electrodes exhibiting acute changes as well as the magnitude of the acute changes in each electrode. The estimation of the location and size of a detected ischemic/infarcted region may also be facilitated by switching to different pacing electrodes in order to change the pacing vector for evoked response electrograms.

Figure 5:
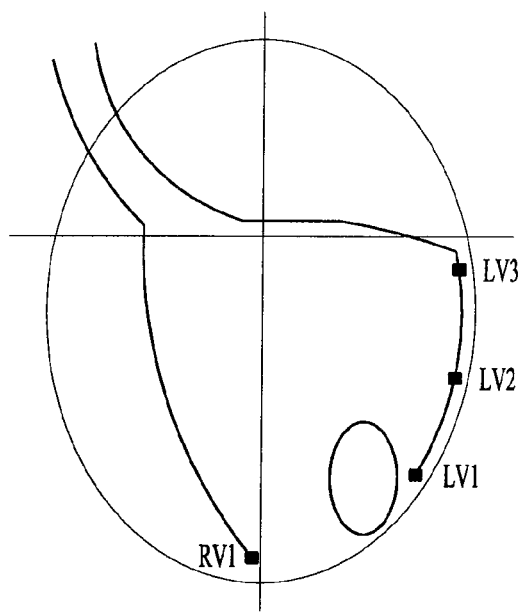
FIG. 5 shows an example of electrode placement in different ventricular regions.
Figure 6:
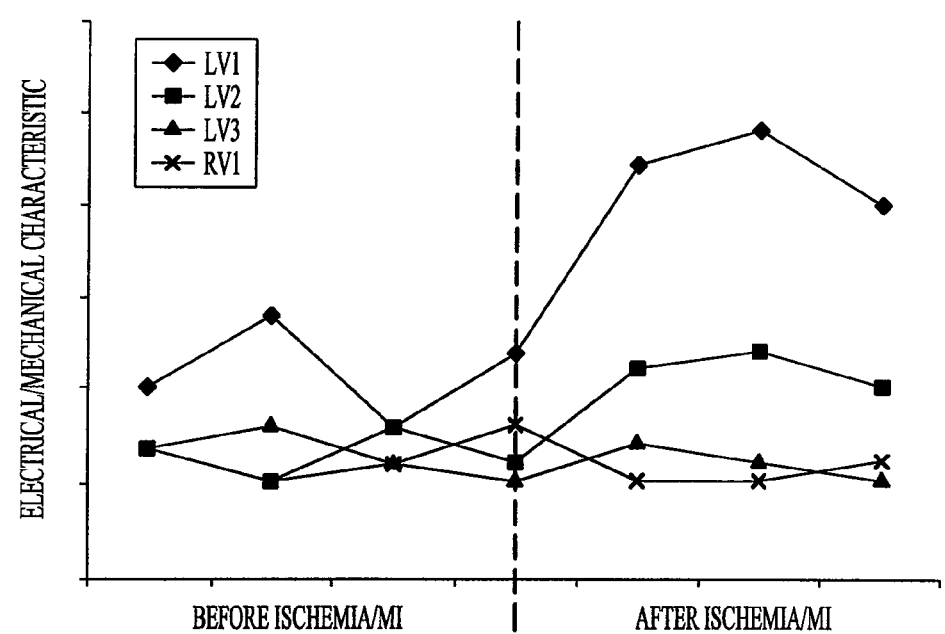
FIG. 6 shows an example of a measured characteristic derived from electrograms generated by the electrodes illustrated in FIG. 5.

FIG. 5 shows an example of four electrodes disposed near different myocardial regions. Electrode RV1 is located in right ventricle near the anterior-apical region, and electrodes LV1 through LV3 are disposed in cardiac veins adjacent the left ventricle to be near the apical-lateral, mid-lateral, and basal-lateral regions, respectively. An area of ischemia or infarction INF is also depicted as located in the apical-lateral region. FIG. 6 shows the time course of an example characteristic derived from electrograms generated by each of the electrodes before and after ischemia or infarction in the apical-lateral region. The characteristic of the electrogram generated by electrode LV1 exhibits an acute change which is assumed to be above its baseline value by an amount sufficient to signal detection of ischemia/infarction. The region of ischemia/infarction is localized to the location of electrode LV1, the apical-lateral region. The size of the ischemic/infarcted region can be estimated from the number of electrodes that exhibit acute changes. In this example, the ischemic/infarcted region can be estimated to be relatively small since electrode LV1 is the only electrode that exhibits acute changes over baseline. A larger area of ischemia/infarction in apical-lateral region, for example, would result in acute changes occurring in the characteristics measured by electrodes RV1 and/or LV2.

Measurement of characteristics for trending in order to establish baseline values may be performed on a periodic basis by the device. Checking for acute changes in the characteristics that would indicate ischemia/infarction may be performed periodically or upon detection of particular conditions or events such as during periods of exertion as detected from heart rate or measured exertion level (e.g., by an accelerometer or minute ventilation sensor), upon detection of particular features in electrogram signals, or upon patient actuation of the magnetically or tactilely actuated switch.

Figure 7:
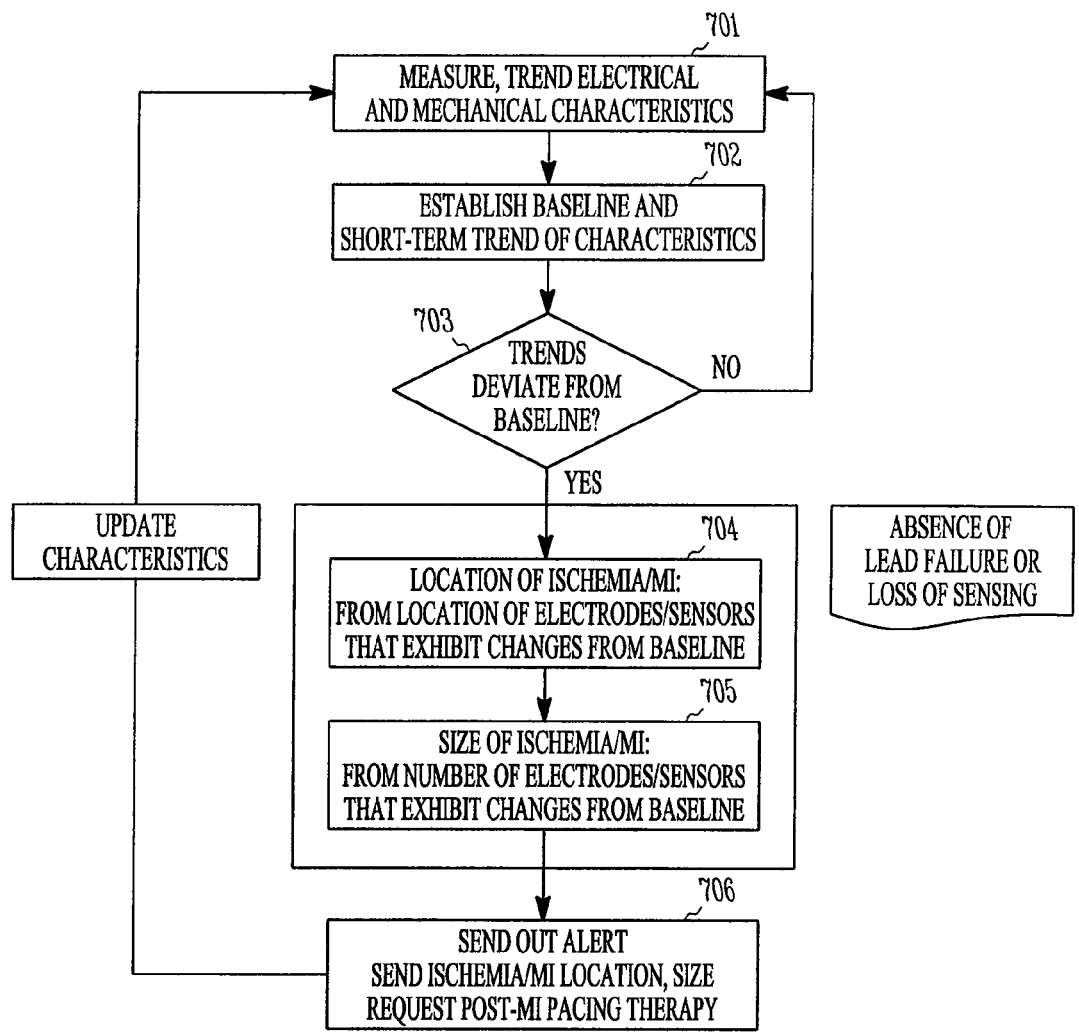
FIG. 7 illustrates an exemplary algorithm for detection and localization of an ischemic/infarcted region.

FIG. 7 illustrates an exemplary algorithm that may be executed by an implantable device to detect, localize, and estimate the size of an ischemic/infarcted region. At step 701, the device measures and trends one or more electrical or mechanical characteristics as derived from signals generated by electrodes or sensors located near different myocardial regions. At step 702, baseline values for the characteristics are established. At step 703, the device checks to see if the trend (s) deviate from the baseline by a specified threshold amount. If not, the device returns to step 701 to continue collecting and trending data. If the characteristics do deviate from the baseline, ischemia/infarction is detected. At step 704, the location of the ischemic/infarcted region is estimated from the location of the electrode(s) that exhibit acute changes from baseline. At step 705, the size of the ischemic/infarcted region is estimated from the number of electrodes that exhibit acute changes from baseline. At step 706, the device transmits an alert message to a remote monitor which may be communicated over a patient management network to clinical personnel so that appropriate therapy may be initiated.

Electrode Reconfiguration to Optimize Pre-Excitation Pacing Therapy

Figure 8:
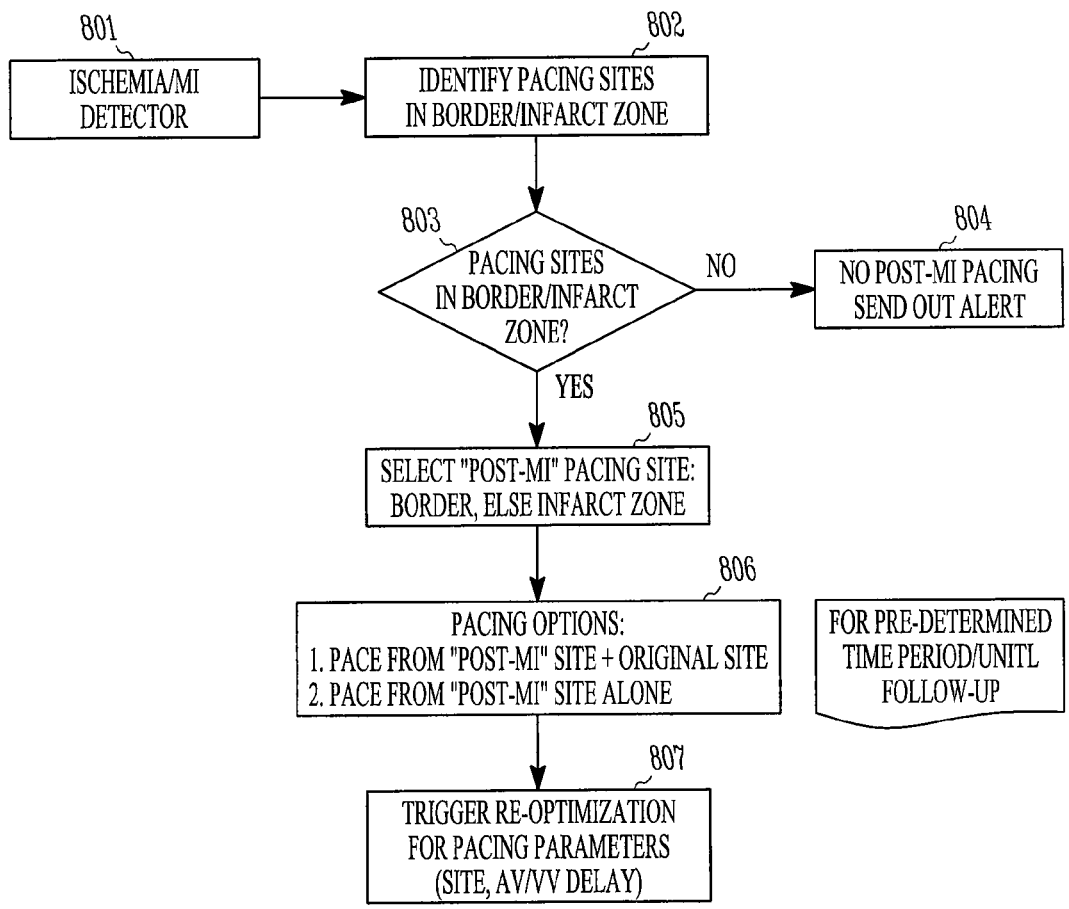
FIG. 8 illustrates an exemplary algorithm for pre-excitation pacing site selection.

If ischemia/infarction is detected and localized as described above in a device capable of delivering pre-excitation pacing therapy, such therapy can be initiated by manual programming of the device or by the device automatically. If the device is already delivering pre-excitation pacing to selected sites, it may be programmed to modify its pre-excitation pacing configuration upon detection and localization of different ischemic/infarcted regions. FIG. 8 illustrates an exemplary algorithm that may be either executed by the device or by a clinician manually programming the device for optimally configuring pre-excitation pacing. At step 801, an ischemic/infarcted region is detected and localized using the device's multiple electrodes as described above. Once an ischemic/infarcted region is identified, an optimal pre-excitation pacing site may be identified as the electrode closest to the affected region in the border zone (i.e., the zone around the affected region) at step 802. The border zone may be identified by combining the electrical and mechanical data from the different electrodes. Next, at step 803, it is determined whether or not there are available pacing sites in either the border zone or the affected region. If it is not certain whether an electrode is in or around the affected region, a pacing pulse can be delivered to that electrode and an evoked response electrogram can be sensed from neighboring electrodes. If the pacing pulse does not pass through to neighboring electrodes, then the electrode can be assumed to be in the affected region. If the border zone cannot be identified, pre-excitation pacing can be attempted to be delivered from an electrode on the affected region. If the affected region cannot be paced either at the affected region itself or at the border zone, or if a pacing electrode is not located within a pre-defined distance from the affected region, no pre-excitation pacing is delivered and an alert message is transmitted at step 804. Otherwise, one or more pacing sites are selected for delivering pre-excitation pacing at step 805. If the identified ischemic/infarcted region is between two electrodes (i.e., two electrodes in the border zone), either or both of the two neighboring electrodes can be used as the pre-excitation site or, alternatively, the neighboring electrode with the larger change in electrogram characteristics from baseline can be selected. If the device is already delivering pacing therapy in the form of conventional bradycardia pacing, resynchronization pacing, or pre-excitation pacing, the device may continue to deliver paces to those original sites in addition to delivering pre-excitation paces to the newly identified sites or may deliver pre-excitation pacing only to the newly identified sites as depicted at step 806. At step 807, a re-optimization algorithm is triggered which may include execution of the pacing electrode reconfiguration algorithm described above using an ordered list updated with the newly identified sites and/or adjustment of pacing parameters such as the AV delay interval.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:
1. An implantable device, comprising:
pulse generation circuitry for generating pacing pulses;
sensing circuitry for receiving electrogram signals;
a switch matrix for connecting the pulse generation circuitry and/or sensing circuitry to electrodes selected from a plurality of electrodes adapted for disposition at a plurality of sites near different myocardial regions;
a controller interfaced to the sensing circuitry that is programmed to derive one or more characteristics from electrogram signals generated by a plurality of electrodes connected to the sensing circuitry by the switch matrix, wherein the one or more characteristics are locally affected by myocardial ischemia or infarction such that the magnitude of a characteristic derived from a particular electrode varies in relation to the proximity of the particular electrode to an ischemic or infarcted myocardial region;

wherein the controller is programmed to measure the one or more characteristics over time and establish baseline values for the measured characteristics;

wherein the controller is programmed to detect myocardial ischemia/infarction when a deviation from the baseline in one or more characteristics occurs above a specified threshold;

wherein the controller is further programmed to localize an ischemic/infarcted region(s) by analyzing the magnitudes of the measured characteristics as derived from differently located electrodes;

wherein the controller is further programmed to, among the plurality of electrodes connected to the sensing circuitry, identify electrodes in a zone around the ischemic/infarcted region and operate the switch matrix to configure a pacing channel with the electrode having the largest change in characteristics above the baseline; and, wherein the controller is further programmed to deliver pre-excitation pacing through the configured pacing channel to a pacing site in proximity to the ischemic/infarcted region.

2. The device of claim 1 wherein the controller is further programmed to adjust an AV delay interval for delivering pre-excitation pacing through the configured pacing channel in an atrial tracking or AV sequential pacing mode.

3. The device of claim 2 wherein the derived characteristic is an intrinsic activation time defined as the time between an atrial pace or sense and a fiducial point extracted from an electrogram.

4. The device of claim 2 wherein the derived characteristic is an electrogram amplitude.

5. The device of claim 2 wherein the derived characteristic is a time interval between the start of depolarization and the end of repolarization in an electrogram signal.

6. The device of claim 2 wherein the derived characteristic is the duration of depolarization in an electrogram signal.

7. The device of claim 2 wherein the derived characteristic is a morphological feature of the electrogram as detected by correlation with a patient-specific template waveform.

8. The device of claim 2 wherein the derived characteristic is a pacing capture threshold.

9. The device of claim 1 further comprising sensors for detecting myocardial displacement or strain and wherein the controller is programmed to derive a characteristic locally affected by ischemia from the sensors.

10. The device of claim 1 wherein the controller is further programmed to localize an ischemic/infarcted region(s) from the number and location of electrodes exhibiting acute changes as well as the magnitude of the acute changes in each electrode.

11. The device of claim 1 wherein the controller is further programmed to issue an alert by transmission of an alert message to a remote monitor via telemetry upon detection of ischemia/infarction.

12. The device of claim 10 wherein the controller is programmed to configure selected ones of the plurality of electrodes into pacing channels for delivering pre-excitation pacing to selected myocardial sites in or around the localized ischemic/infarcted region.

13. A method, comprising:

receiving electrogram signals from a plurality of electrodes disposed near different myocardial regions;

deriving one or more characteristics from the electrogram signals, wherein the one or more characteristics are locally affected by myocardial ischemia or infarction such that the magnitude of a characteristic derived from a particular sensor varies in relation to the proximity of the particular electrode to an ischemic or infarcted myocardial region;

measuring the one or more characteristics over time and establish baseline values for the measured characteristics;

detecting myocardial ischemia/infarction when a deviation from the baseline in one or more characteristics occurs above a specified threshold;

localizing an ischemic/infarcted region(s) by analyzing the magnitudes of the measured characteristics as derived from differently located electrodes;

identifying electrodes in a zone around the ischemic/infarcted region and operating a switch matrix to configure a pacing channel with the electrode having the largest change in characteristics above the baseline; and, delivering pre-excitation pacing to a pacing site in proximity to the ischemic/infarcted region through the configured pacing channel.

14. The method of claim 13 further comprising adjusting an AV delay interval for delivering pre-excitation pacing through the configured pacing channel in an atrial tracking or AV sequential pacing mode.

15. The method of claim 14 wherein the derived characteristic is an intrinsic activation time defined as the time between an atrial pace or sense and a fiducial point extracted from an electrogram.

16. The method of claim 14 wherein the derived characteristic is an electrogram amplitude.

17. The method of claim 14 wherein the derived characteristic is a time interval between the start of depolarization and the end of repolarization in an electrogram signal.

18. The method of claim 14 wherein the derived characteristic is the duration of depolarization in an electrogram signal.

19. The method of claim 14 wherein the derived characteristic is a morphological feature of the electrogram as detected by correlation with a patient-specific template waveform.

20. The method of claim 14 further comprising localizing an ischemic/infarcted region(s) from the number and location of electrodes exhibiting acute changes as well as the magnitude of the acute changes in each electrode.

* * * * *